(12) United States Patent
Altman

(10) Patent No.: US 8,956,590 B2
(45) Date of Patent: Feb. 17, 2015

(54) COMPOSITIONS AND METHODS FOR REDUCING THE INCIDENCE OF EQUINE DIGESTIVE DISORDERS

(75) Inventor: Jay A. Altman, St. Louis, MO (US)

(73) Assignee: Altera International, Ltd., Fort Collins, CO (US)

(*) Notice: Subject to any disclaimer, the term of this patent is extended or adjusted under 35 U.S.C. 154(b) by 0 days.

(21) Appl. No.: 13/554,494

(22) Filed: Jul. 20, 2012

(65) Prior Publication Data

US 2013/0022576 A1 Jan. 24, 2013

Related U.S. Application Data

(60) Provisional application No. 61/510,793, filed on Jul. 22, 2011.

(51) Int. Cl.
| | |
|---|---|
| *A61K 49/00* | (2006.01) |
| *A61K 36/064* | (2006.01) |
| *A61K 38/47* | (2006.01) |
| *A61K 38/48* | (2006.01) |
| *A61K 36/38* | (2006.01) |

(52) U.S. Cl.
CPC .............. *A61K 35/744* (2013.01); *A61K 36/064* (2013.01); *A61K 38/47* (2013.01); *A61K 38/48* (2013.01); *A61K 35/747* (2013.01); *A61K 36/38* (2013.01); *C12Y 304/00* (2013.01); *C12Y 302/01001* (2013.01); *C12Y 302/01004* (2013.01)
USPC ........................... 424/9.1; 424/93.1; 424/93.3

(58) Field of Classification Search
USPC .................................. 424/9.1, 93.1
See application file for complete search history.

(56) References Cited

U.S. PATENT DOCUMENTS

| 7,595,079 B2 | 9/2009 | Lall | |
|---|---|---|---|
| 2007/0298013 A1* | 12/2007 | Altman | 424/93.3 |
| 2009/0297481 A1* | 12/2009 | Powlen | 424/93.3 |
| 2010/0021430 A1* | 1/2010 | Baginski | 424/93.3 |

OTHER PUBLICATIONS

Arenus, http://www.arenus.com/products/assure/assure-guard.php (last visited Aug. 7, 2013).*
Google Search (last visited Aug. 2, 2013).*
Google Search (last visited Aug. 9, 2013).*
Assure System, http:/www.emsvet.com/newsletters/digestive/assure-products.html (last visited Aug. 9, 2013), Digestive Horse Health Newsletter Articles—Equine Medical Service, May 5, 2009.*
Landes et al., Fecal Sand Clearance is Enhanced with a Product Combining Probiotics, Prebiotics, and Psyllium in Clinically Normal Horses, Journal of Equine Veterinary Science, vol. 28, No. 2, (2008).*
International Search Report and Written Opinion dated Jan. 22, 2013 from related International Appln. No. PCT/US2012/047634.
Landes, Fecal Sand Clearance is Enhanced with a Product Combining Probiotics, Prebiotics, and Psyllium in Clinically Normal Horses, Journal of Equine Veterinary Science, 20080, vol. 28(2):79-84.
Arenus, Assure, Horse Nutritional Supplements for Equine Health, Dec. 27, 2010, downloaded from http://web.archive.org/web/20101220134102/http://shop.arenus.com/p-12assure.aspx on Oct. 17, 2010; p. 3-8.
Arenus, Assure Plus Equine Sand Clearance Supplement to Reduce Horse Digestive colic, Dec. 27, 2010, downloaded from http://web.archive.org/web/20101227034410/http://shop.arenus.com/p-16-assure-plus.aspx on Oct. 17, 2012; p. 3-8.
Arenus, Assure Guard, Horse Digestive Supplemental Support Hindgut Mobility, Oct. 13, 2010, downloaded from: http://web.archive.org/web/20101013220842/http://shop.arenus.com/p-14-assure-guard.aspx on Oct. 17, 2012, p. 3-8.
Invitation to Pay Additional Fees communication dated Nov. 8, 2012 from related International application No. PCT/US2012/047634, 3 pgs.
Landes, Fecal Sand Clearance Is Enhanced with a Product Combining Probiotics, Prebiotics, and Psyllium in Clinically Normal Hourses, Journal of Equine Veterinary Science, 2008, pp. 79-84, vol. 28, No. 2.

* cited by examiner

*Primary Examiner* — Bin Shen
(74) *Attorney, Agent, or Firm* — Polsinelli PC

(57) ABSTRACT

The present invention encompasses compositions and methods of reducing the incidence of equine digestive disorders. A combination of either composition A (ASSURE PLUS®) and composition B (ASSURE®) or a combination of composition A (ASSURE PLUS®) and composition C (ASSURE GUARD®) may be administered to the equine.

17 Claims, No Drawings

COMPOSITIONS AND METHODS FOR REDUCING THE INCIDENCE OF EQUINE DIGESTIVE DISORDERS

CROSS REFERENCE TO RELATED APPLICATIONS

This application claims the priority of U.S. Provisional Application No. 61/510,793, filed Jul. 22, 2011, which is hereby incorporated by reference in its entirety.

FIELD OF THE INVENTION

The invention encompasses compositions and methods for reducing the incidence of equine digestive disorders.

BACKGROUND OF THE INVENTION

Digestive upset in the horse has become commonplace. The intensity of modern feeding and management changes has contributed to a subset of the population of horses with frequent if not constant digestive upset. Many horses are being fed an abundance of concentrated feeds that adds additional physiologic stress to a digestive system that is not performing as designed. The veterinary practitioner often encounters horses suffering with one or more of the following conditions, gastric ulcers, recurrent diarrhea, recurrent colic, weight loss, poor condition and sand accumulation.

Colic in particular is a leading cause of equine death. While certain treatments are available for acute colic (such as administration of analgesics, administration of mineral oil or other lubricants/laxatives, relieving pressure on the stomach with a nasalgastric tube, administration of intravenous fluids, surgery, etc.) managing an equine who suffers from multiple colic episodes over a period of time is much more challenging. General treatment strategies include evaluating management parameters, such as feed (quality, quantity, balance, etc.), stabling/pasturing conditions, and deworming program, and making any appropriate changes. If the colic is refractory to these management changes, there are no known treatment alternatives.

Hence, there is a need in the art for compositions and methods of treating equine digestive disorders.

SUMMARY OF THE INVENTION

One aspect of the present invention encompasses a method for reducing the incidence of recurrent colic in an equine, the method comprising identifying an equine in need of treatment for recurrent colic and administering a combination of composition A and composition B to the equine.

Another aspect of the present invention encompasses a method for reducing the incidence of recurrent colic in an equine, the method comprising identifying an equine in need of treatment for recurrent colic and administering a combination of composition A and composition C to the equine.

Yet another aspect of the present invention encompasses a method for reducing the incidence of recurrent diarrhea in an equine, the method comprising identifying an equine in need of treatment for recurrent diarrhea and administering a combination of composition A and composition B to the equine.

Still another aspect of the present invention encompasses a method for reducing the incidence of recurrent diarrhea in an equine, the method comprising identifying an equine in need of treatment for recurrent diarrhea and administering a combination of composition A and composition C to the equine.

An alternative aspect of the present invention encompasses a method for normalizing intestinal motility in an equine, the method comprising identifying an equine in need of treatment for intestinal hypermotility or hypomotility and administering a combination of composition A and composition B to the equine.

Another alternative aspect of the present invention encompasses a method for normalizing intestinal motility in an equine, the method comprising identifying an equine in need of treatment for intestinal hypermotility or hypomotility and administering a combination of composition A and composition C to the equine.

Other aspects and iterations of the invention are described more thoroughly below.

DETAILED DESCRIPTION OF THE INVENTION

The present invention provides methods of reducing the incidence of equine digestive disorders. In particular embodiments, the present invention provides methods of reducing or eliminating recurrent digestive disorders. In additional embodiments, the present invention provides methods of normalizing equine intestinal motility. Generally speaking, such methods comprise daily administration of a combination of either composition A and B, or a combination of composition A and C. Each of the compositions are detailed in section I below, and the methods of the invention are described in section II below.

I. Compositions

The methods of the invention comprise daily administration of a combination of either composition A and composition B or a combination of composition A and composition C according to the details below. A composition or combination of the invention may be formulated as a pellet, crumble, flake, powder, granule, tablet, liquid, paste, solution, or any other suitable form. Generally speaking, a composition or combination may be administered as a feed additive, syringed by mouth, or pasted by mouth.

(a) Composition A

Composition A is comprised of soluble fiber, live microorganisms, active enzymes, and optionally, additional components. Each component is discussed in more detail below.

i. Soluble Fiber

Composition A comprises, in part, soluble fiber. Generally speaking the amount of soluble fiber of composition A is between about 60% and about 90%. Suitable sources of soluble fiber are known in the art, and non-limiting examples may include psyllium seed husk, beet pulp, and soybean hulls. In an exemplary embodiment, the soluble fiber of composition A comprises psyllium seed husk. In one embodiment, the amount of psyllium seed husk is adjusted so that the soluble fiber of composition A is about 60, 65, 70, 75, 80, 85% or 90%. In an exemplary embodiment, the amount of psyllium seed husk is adjusted so that the soluble fiber of composition A is about 70, 71, 72, 73, 74 or 75%. Methods of determining the soluble fiber in a composition are known in the art.

ii. Live Microorganisms

Generally speaking, composition A is comprised of at least two types of live microorganisms: a yeast and a bacteria strain. Suitable yeast may include a *Saccharomyces* species, such as *Saccharomyces bayanus, Saccharomyces boulardii, Saccharomyces bulderi, Saccharomyces cariocanus, Saccha-* romyces cariocus, Saccharomyces cerevisiae, Saccharomyces chevalieri, Saccharomyces dairenensis, Saccharomyces ellipsoideus, Saccharomyces exiguous, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum, or Saccharomyces zonatus. In an exemplary embodiment, composition A comprises Saccharomyces cerevisiae. Suitable yeast may also comprise yeast from species and/or genera other than Saccharomyces.

Composition A may comprise one, two, three or more than three yeast species. Regardless of the number of number of yeast species, the concentration of yeast in composition A may be between about 60 million cfu/g to about 1 billion cfu/g yeast. In one embodiment, the concentration of yeast in composition A is between about 60, 70, 75, 80, 85, 90, 95, or about 100 million cfu/g. In an exemplary embodiment, the concentration of yeast in composition A is between about 75 million cfu of yeast to about 85 million cfu of yeast per gram of composition A.

Composition A is also comprised of at least one bacterial strain. Suitable bacterial strains may include a Lactobacillus species, an Enterococcus species, a Bifidobacterium species, a Propionibacterium species, a Streptococcus species, a Bacillus species, or a Pediococcus species.

For instance, suitable Lactobacillus species may include Lactobacillus acidophilus, Lactobacillus casei, Lactobacillus salivarius, Lactobacillus plantarum, Lactobacillus Lactis, Lactobacillus rhamnosus, Lactobacillus rhamnosus, Lactobacillus pentosus, Lactobacillus reuteri, Lactobacillus crispatus, Lactobacillus johnsonii, and Lactobacillus equi. In an exemplary embodiment, the Lactobacillus species is Lactobacillus acidophilus.

Suitable Enterococcus species may include Enterococcus faecium, Enterococcus avium, Enterococcus durans, Enterococcus faecalis, Enterococcus faecium, Enterococcus gallinarum, and Enterococcus solitarius. In an exemplary embodiment, the Enterococcus species is Enterococcus faecium.

Additionally, suitable Bacillus species may include Bacillus subtilis, Bacillus pumilus, and Bacillus lichenformis. Suitable Streptococcus species may include Streptococcus Cremoris or Streptococcus Diacetilactis. Suitable Propionibacterium species may include Propionibacterium freudenreichii. Suitable Bifidobacterium species may include Bifidobacterium longum and Bifidobacterium lactis. Suitable Pediococcus species may include Pediococcus acidilactici.

Composition A may comprise one, two, three, four, five, or more than five bacterial species. In an exemplary embodiment, composition A comprises at least one Lactobacillus species and at least one Enterococcus species. In a further exemplary embodiment, composition A comprises Lactobacillus acidophilus and Enterococcus faecium. When composition A comprises Lactobacillus acidophilus, composition A comprises between about 2 million cfu/g to about 40 million cfu/g Lactobacillus acidophilus. In another exemplary embodiment, composition A comprises about 2 million cfu/g to about 30 million cfu/g Lactobacillus acidophilus. In yet another exemplary embodiment, composition A comprises about 2 million cfu/g to about 20 million cfu/g Lactobacillus acidophilus. In still another exemplary embodiment, composition A comprises about 2 million cfu/g to about 10 million cfu/g Lactobacillus acidophilus. In an additional exemplary embodiment, composition A comprises about 2, 3, 4, 5, 6, 7, 8, 9, or 10 million cfu/g Lactobacillus acidophilus.

When composition A comprises Enterococcus faecium, composition A comprises between about 2 million cfu/g to about 40 million cfu/g. In another exemplary embodiment, composition A comprises about 2 million cfu/g to about 30 million cfu/g Enterococcus faecium. In yet another exemplary embodiment, composition A comprises about 2 million cfu/g to about 20 million cfu/g Enterococcus faecium. In still another exemplary embodiment, composition A comprises about 2 million cfu/g to about 10 million cfu/g Enterococcus faecium. In an additional exemplary embodiment, composition A comprises about 2, 3, 4, 5, 6, 7, 8, 9, or 10 million cfu/g Enterococcus faecium.

In a preferred embodiment, composition A comprises between about 2 million and about 10 million cfu/g Lactobacillus acidophilus, and between about 2 million and about 10 million cfu/g Enterococcus faecium.

iii. Active Enzyme

Composition A also comprises at least one active enzyme. In some embodiments, composition A comprises at least one, two, three, four, or more than four active enzymes. Suitable active enzymes include those useful for digesting nutrients, including proteases, amylases, cellulases, lipases, etc. For instance, composition A may comprise a protease, an alpha-amylase, and a cellulase. Methods of producing and/or procuring such active enzymes are known in the art. For instance, the enzymes may be commercially produced, may be recombinantly produced, or may be derived from a microbial culture.

In one embodiment, composition A comprises a protease. In a preferred embodiment, composition A comprises a protease derived from an Aspergillus culture. Suitable Aspergillus species may include Aspergillus oryzae, Aspergillus ficuum (Aspergillus niger), or another protease producing strain of Aspergillus. In an exemplary embodiment, composition A comprises a protease derived from Aspergillus oryzae. In another exemplary embodiment, composition A comprises between about 0.8 HUT/g (hemoglobin units on tyrosine beads/g) to about 1.2 HUT/g of protease derived from Aspergillus oryzae.

In another embodiment, composition A comprises an alpha-amylase. In a preferred embodiment, composition A comprises an alpha-amylase derived from a Bacillus culture. Suitable Bacillus strains may include those listed in section I(a)i above. In an exemplary embodiment, composition A comprises an alpha-amylase from Bacillus subtilis. In another exemplary embodiment, composition A comprises between about 2.5 to about 3.5 MWU/g (modified Wohlgemuth units) of alpha-amylase derived from Bacillus subtilis.

In yet another embodiment, composition A comprises a cellulase. In a preferred embodiment, composition A comprises a cellulase derived from a Trichoderma culture. Suitable Trichoderma strains may include Trichoderma longibrachiatum or Trichoderma reesei. In an exemplary embodiment, composition A comprises a cellulase derived from Trichoderma longibrachiatum. In another exemplary embodiment, composition A comprises between about 0.2 to about 0.6 CU/g (cellulase units/g) of cellulase derived from Trichoderma longibrachiatum.

In an exemplary embodiment, composition A comprises a protease derived from Aspergillus oryzae, an alpha-amylase from Bacillus subtillis, and a cellulase from Trichoderma longibrachiatum. In a further exemplary embodiment, composition A comprises between about 0.8 HUT/g (hemoglobin units on tyrosine beads/g) to about 1.2 HUT/g of protease derived from Aspergillus oryzae, between about 2.5 to about 3.5 MWU/g (modified Wohlgemuth units) of alpha-amylase derived from *Bacillus subtilis*, and between about 0.2 to about 0.6 CU/g (cellulase units/g) of cellulase derived from *Trichoderma longibrachiatum*.

iv. Other Components

Composition A may further comprise fillers, binders, sweeteners, smectite, anti-caking agents, natural or artificial flavorings, or similar inert ingredients. Non-limiting examples of suitable fill or binding agents may include lignin-based binding agents, molasses-based binding agents, calcium bentonite binding agents, gelatins, soy-based lecithin, casein, gluten, cellulose, wheat millrun and aqueous solutions. Suitable sweeteners may include natural sweeteners such as molasses and simple sugars such as sucrose and dextrose. Artificial sweeteners such as saccharin-based sweeteners, aspartame and sorbitol (glucitol) may also be employed. Equine have shown a tolerance for vanilla, licorice, cherry, citrus and apple flavoring. However, other flavoring may also be selected if desired. Secondary flavorings may be used as enhancing agents. For example, a combination of dry flavors and oil-based flavors may be used for extended aroma properties over the course of the product's recommended shelf-life.

In some embodiments, composition A may comprise sodium calcium aluminosilicates. In other embodiments, composition A may comprise yeast cell wall extracts. For instance, composition A may comprise dried yeast fermentation solubles. In various embodiments, composition A may comprise one or more prebiotics. In one embodiment, composition A may comprise ZORIEN® Mos (yeast feed additive containing mannanoligosaccharides), manufactured by Novus® International.

In certain embodiments, composition A may include smectite. Smectite may either be dioctahedral smectite, trioctahedral smectite or a combination of both which is commonly known as DTO Smectite (Di, Tri Octahedral). Smectite may aid in reducing detrimental bacterial toxins in the colon. In some embodiments, composition A may comprise from about 10% to about 70% by weight of smectite.

v. Crude Analysis

Composition A comprises crude protein from at least about 2% to about 20%. In some embodiments, composition A comprises crude protein from at least about 2, 3, 4, 5, 6, 7, 8, 9, 10, 11, 12, 13, 14, 15, 16, 17, 18, 19, or 20%. In an exemplary embodiment, the crude protein is at least from about 2% to about 6%. Typically, composition A comprises a crude fat amount of at least about 0.5% to about 5%. In particular embodiments, composition A comprises crude fat of at least about 0.5, 1.0, 1.5, 2.0, 2.5, 3.0, 3.5, 4.0, 4.5, or 5.0%. In an exemplary embodiment, the crude fat amount is at least between about 0.5% and 1.5%. The crude fiber in composition A is usually between about 2% and about 15%. In certain embodiments, composition A comprises a crude fiber amount of less than about 2, 3, 4, 5, 6, 7, 8, 9, 10, 11, 12, 13, 14, or 15%. In an exemplary embodiment, the crude fiber amount is between about 6% and 10%.

In a particularly exemplary embodiment, composition A comprises between about 2% to about 6% crude protein, between about 0.5% and 1.5% crude fat, and between about 6% and 10% crude fiber.

vi. Exemplary Embodiments

In an exemplary embodiment, composition A comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk.

In a further exemplary embodiment, composition A comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber.

In yet another exemplary embodiment, composition A comprises psyllium seed husk, wheat mill run, molasses, dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, Brewers dried yeast, dried *Saccharomyces cerevisiae* fermentation solubles, and natural and artificial flavoring, wherein the composition comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber.

In a preferred embodiment, composition A comprises ASSURE PLUS® (equine digestive supplement), which is commercially available through Arenus®, a Novus International Business.

vii. Dosage and Administration

Composition A is generally administered at a daily dosage of between about 0.10 g/lb and about 0.70 g/lb for a solid formulation. In some embodiments, composition A is generally administered at a daily dosage of about 0.10, 0.20, 0.30, 0.40, 0.50, 0.60, or 0.70 g/lb for a solid formulation. In an alternative embodiment, a paste formulation of composition A may be administered at a dosage between about 0.01 g/lb to about 0.2 g/lb. For instance, a paste formulation may be administered at a dosage of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.20 g/lb. Dosages depend, in part, on various factors including general health of the equine, weight, age, and state of nutrition. Dosages may also depend on the formulation of the composition. As a result, one of skill in the art will appreciate that the dosages described herein can and will vary.

Generally speaking, composition A may be administered in two phases. In the first phase, composition A is administered daily for at least two weeks, and preferably more than three weeks. In one embodiment, in the first phase, composition A is administered daily for four weeks. In another first phase embodiment, composition A is administered daily for five weeks. In the second phase, which repeats, composition A is not feed for three weeks, followed by a week of daily administration. Stated another way, in the second phase, composition A is administered daily for one week a month.

In certain embodiments where the digestive disorder is particularly severe, composition A may be administered twice a day. In these embodiments, twice a day administration may be used until the desired improvement in equine condition is observed, after which the two phase administration detailed above may be employed.

(b) Composition B

Composition B is comprised of live microorganisms, active enzymes, and optionally, additional components, such as soluble fiber. Each component is discussed in more detail below.

i. Live Microorganisms

Generally speaking, composition B is comprised of at least two types of live microorganisms: a yeast and a bacteria strain. Suitable yeast may include a *Saccharomyces* species, such as *Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces exiguous, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum*, or *Saccharomyces zonatus*. In an exemplary embodiment, composition B comprises *Saccharomyces cerevisiae*. Suitable yeast may also comprise yeast from species and/or genera other than *Saccharomyces*.

Composition B may comprise one, two, three or more than three yeast species. Regardless of the number of number of yeast species, the concentration of yeast in composition B is between about 800 million cfu/g to about 1.4 billion cfu/g yeast. In one embodiment, the concentration of yeast in composition B is about 800, 900, 1000, 1100, 1200, 1300, or about 1400 million cfu/g. In an exemplary embodiment, the concentration of yeast in composition B is between about 1000 million cfu of yeast to about 1200 million cfu of yeast per gram of composition B.

Composition B is also comprised of at least one bacterial strain. Suitable bacterial strains may include a *Lactobacillus* species, an *Enterococcus* species, a *Bifidobacterium* species, a *Propionibacterium* species, a *Streptococcus* species, a *Bacillus* species, or a *Pediococcus* species.

For instance, suitable *Lactobacillus* species may include *Lactobacillus acidophilus, Lactobacillus casei, Lactobacillus salivarius, Lactobacillus plantarum, Lactobacillus Lactis, Lactobacillus rhamnosus, Lactobacillus rhamnosus, Lactobacillus pentosus, Lactobacillus reuteri, Lactobacillus crispatus, Lactobacillus johnsonii,* and *Lactobacillus equi*. In an exemplary embodiment, the *Lactobacillus* species is *Lactobacillus acidophilus*.

Suitable *Enterococcus* species may include *Enterococcus faecium, Enterococcus avium, Enterococcus durans, Enterococcus faecalis, Enterococcus faecium, Enterococcus gallinarum,* and *Enterococcus solitarius*. In an exemplary embodiment, the *Enterococcus* species is *Enterococcus faecium*.

Additionally, suitable *Bacillus* species may include *Bacillus subtilis, Bacillus pumilus,* and *Bacillus lichenformis*. Suitable *Streptococcus* species may include *Streptococcus Cremoris* or *Streptococcus Diacetilactis*. Suitable *Propionibacterium* species may include *Propionibacterium freudenreichii*. Suitable *Bifidobacterium* species may include *Bifidobacterium longum* and *Bifidobacterium lactis*. Suitable *Pediococcus* species may include *Pediococcus acidilactici*.

Composition B may comprise one, two, three, four, five, or more than five bacterial species. In an exemplary embodiment, composition B comprises at least one *Lactobacillus* species and at least one *Enterococcus* species. In a further exemplary embodiment, composition B comprises *Lactobacillus acidophilus* and *Enterococcus faecium*. When composition B comprises *Lactobacillus acidophilus*, composition B comprises between about 45 million cfu/g to about 85 million cfu/g *Lactobacillus acidophilus*. In another exemplary embodiment, composition B comprises about 50 million cfu/g to about 80 million cfu/g *Lactobacillus acidophilus*. In yet another exemplary embodiment, composition B comprises about 55 million cfu/g to about 75 million cfu/g *Lactobacillus acidophilus*. In still another exemplary embodiment, composition B comprises about 60 million cfu/g to about 70 million cfu/g *Lactobacillus acidophilus*. In an some exemplary embodiments, composition B comprises about 260, 61, 62, 63, 64, 65, 66, 67, 68, 69, or 70 million cfu/g *Lactobacillus acidophilus*.

When composition B comprises *Enterococcus faecium*, composition B comprises between about 20 million cfu/g to about 60 million cfu/g. In another exemplary embodiment, composition B comprises about 25 million cfu/g to about 55 million cfu/g *Enterococcus faecium*. In yet another exemplary embodiment, composition B comprises about 30 million cfu/g to about 50 million cfu/g *Enterococcus faecium*. In still another exemplary embodiment, composition B comprises about 40 million cfu/g to about 50 million cfu/g *Enterococcus faecium*. In an additional exemplary embodiment, composition B comprises about 40, 41, 42, 43, 44, 45, 46, 47, 48, 49 or 50 million cfu/g *Enterococcus faecium*.

In a preferred embodiment, composition B comprises between about 60 million and about 70 million cfu/g *Lactobacillus acidophilus*, and between about 40 million and about 50 million cfu/g *Enterococcus faecium*.

ii. Active Enzyme

Composition B also comprises at least one active enzyme. In some embodiments, composition B comprises at least one, two, three, four, or more than four active enzymes. Suitable active enzymes include those useful for digesting nutrients, including proteases, amylases, cellulases, lipases etc. For instance, composition B may comprise a protease, an alpha-amylase, and a cellulase. Methods of producing and/or procuring such active enzymes are known in the art. For instance, the enzymes may be commercially produced, may be recombinantly produced, or may be derived from a microbial culture.

In one embodiment, composition B comprises a protease. In a preferred embodiment, composition B comprises a protease derived from an *Aspergillus* culture. Suitable *Aspergillus* species may include *Aspergillus oryzae, Aspergillus ficuum (Aspergillus niger)*, or another protease producing strain of *Aspergillus*. In an exemplary embodiment, composition B comprises a protease derived from *Aspergillus oryzae*. In another exemplary embodiment, composition B comprises between about 10 HUT/g (hemoglobin units on tyrosine beads/g) to about 15 HUT/g of protease derived from *Aspergillus oryzae*. In yet another exemplary embodiment, composition B comprises between about 12 HUT/g to about 14 HUT/g of protease derived from *Aspergillus oryzae*.

In another embodiment, composition B comprises an alpha-amylase. In a preferred embodiment, composition B comprises an alpha-amylase derived from a *Bacillus* culture. Suitable *Bacillus* strains may include those listed in section I(a)i above. In an exemplary embodiment, composition B comprises an alpha-amylase from *Bacillus subtilis*. In another exemplary embodiment, composition B comprises between about 35 and about 55 MWU/g (modified Wohlgemuth units) of alpha-amylase derived from *Bacillus subtilis*. In yet another exemplary embodiment, composition B comprises between about 40 and about 50 MWU/g of alpha-amylase derived from *Bacillus subtilis*.

In yet another embodiment, composition B comprises a cellulase. In a preferred embodiment, composition B comprises a cellulase derived from a *Trichoderma* culture. Suitable *Trichoderma* strains may include *Trichoderma longibrachiatum* or *Trichoderma reesei*. In an exemplary embodiment, composition B comprises a cellulase derived from *Trichoderma longibrachiatum*. In another exemplary embodiment, composition B comprises between about 4 to about 8 CU/g (cellulase units/g) of cellulase derived from *Trichoderma longibrachiatum*. In yet another exemplary embodiment, composition B comprises between about 5 to about 7 CU/g of cellulase derived from *Trichoderma longibrachiatum*.

In an exemplary embodiment, composition B comprises a protease derived from *Aspergillus oryzae*, an alpha-amylase from *Bacillus subtillis*, and a cellulase from *Trichoderma longibrachiatum*. In a further exemplary embodiment, composition B comprises between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, and between about 5 to about 7 CU/g (cellulase units/g) of cellulase derived from *Trichoderma longibrachiatum*.

iii. Other Components

Composition B may further comprise fillers, binders, sweetners, smectite, anti-caking agents, natural or artificial flavorings, or similar inert ingredients. Examples of suitable fill or binding agents may include lignin-based binding agents, molasses-based binding agents, calcium bentonite binding agents, gelatins, soy-based lecithin, casein, gluten, cellulose, wheat millrun and aqueous solutions. Suitable sweeteners may include natural sweeteners such as molasses and simple sugars such as sucrose and dextrose. Artificial sweeteners such as saccharin-based sweeteners, aspartame and sorbitol (glucitol) may also be employed. Equine have shown a tolerance for vanilla, licorice, cherry, citrus and apple flavoring. However, other flavoring may also be selected if desired. Secondary flavorings may be used as enhancing agents. For example, a combination of dry flavors and oil-based flavors may be used for extended aroma properties over the course of the product's recommended shelf-life.

In some embodiments, composition B may comprise sodium calcium aluminosilicates. In other embodiments, composition B may comprise yeast cell wall extracts. For instance, composition B may comprise dried yeast fermentation solubles. In various embodiments, composition B may comprise one or more prebiotics. In one embodiment, composition B may comprise ZORIEN® Mos, manufactured by Novus® International.

As noted above, composition B also may comprise soluble fiber. Suitable sources of soluble fiber are known in the art, and non-limiting examples may include psyllium seed husk, beet pulp, and soybean hulls. In an exemplary embodiment, the soluble fiber of composition B comprises psyllium seed husk. In one embodiment, composition B comprises between about 5% and 20% by weight psyllium seed husk. For instance, composition B may comprise about 5, 6, 7, 8, 9, 10, 11, 12, 13, 14, 15, 16, 17, 18, 19, or 20% psyllium seed husk by weight.

In other embodiments, composition B may include smectite. Smectite may either be dioctahedral smectite, trioctahedral smectite or a combination of both which is commonly known as DTO Smectite (Di, Tri Octahedral). Smectite may aid in reducing detrimental bacterial toxins in the colon. In some embodiments, composition B may comprise from about 10% to about 70% by weight of smectite.

In further embodiments, composition B may include biotin, gelatin, minerals, such as zinc, copper, amino acids, such as methionine or lysine, and vitamins, such as pyridoxine.

iv. Crude Analysis

Composition B comprises crude protein from at least about 2% to about 20%. In some embodiments, composition A comprises crude protein from at least about 2, 3, 4, 5, 6, 7, 8, 9, 10, 11, 12, 13, 14, 15, 16, 17, 18, 19, or 20%. In an exemplary embodiment, the crude protein is from at least about 6% to about 10%. Typically, composition B comprises a crude fat amount of at least about 0.5% to about 5%. In particular embodiments, composition B comprises crude fat of at least about 0.5, 1.0, 1.5, 2.0, 2.5, 3.0, 3.5, 4.0, 4.5, or 5.0%. In an exemplary embodiment, the crude fat amount is between about 0.5% and 1.5%. The crude fiber in composition B is usually between about 2% and about 15%. In certain embodiments, composition B comprises a crude fiber amount of about 2, 3, 4, 5, 6, 7, 8, 9, 10, 11, 12, 13, 14, or 15%. In an exemplary embodiment, the crude fiber amount is between about 4% and 8%.

In a particularly exemplary embodiment, composition B comprises between about 6% to about 10% crude protein, between about 0.5% and 1.5% crude fat, and between about 4% and 8% crude fiber.

v. Exemplary Embodiments

In an exemplary embodiment, composition B comprises between about 1000 million cfu of yeast to about 1200 million cfu of yeast per gram of composition A, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7

CU/g (cellulase units/g) of cellulase derived from *Trichoderma longibrachiatum*, and psyllium seed husk.

In a further exemplary embodiment, composition B comprises between about 1000 million cfu of yeast to about 1200 million cfu of yeast per gram of composition B, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7 CU/g (cellulase units/g) of cellulase derived from *Trichoderma longibrachiatum*, and psyllium seed husk, such that composition B comprises between about 6% to about 10% crude protein, between about 0.5% and 1.5% crude fat, and between about 4% and 8% crude fiber.

In yet another exemplary embodiment, composition B comprises dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, Brewers dried yeast, dried *Saccharomyces cerevisiae* fermentation solubles, psyllium seed husk, and natural and artificial flavoring, wherein the composition comprises between about 1000 million cfu of yeast to about 1200 million cfu of yeast per gram of composition B, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7 CU/g (cellulase units/g) of cellulase derived from *Trichoderma longibrachiatum*, and psyllium seed husk, such that composition B comprises between about 6% to about 10% crude protein, between about 0.5% and 1.5% crude fat, and between about 4% and 8% crude fiber.

In a preferred embodiment, composition B comprises ASSURE® (equine digestive supplement), which is commercially available through Arenus®, a Novus International Business. In some embodiments, composition B may be ASSURE HOOF® (equine digestive supplement), also commercially available through Arenus®.

vi. Dosage and Administration

Composition B is generally administered at a daily dosage of between about 0.010 g/lb and about 0.06 g/lb for a solid formulation. In some embodiments, composition B is generally administered at a daily dosage of about 0.010, 0.020, 0.030, 0.040, 0.050, or 0.060 g/lb for a solid formulation. In an alternative embodiment, a paste formulation of composition B may be administered at a dosage between about 0.01 g/lb to about 0.2 g/lb. For instance, a paste formulation may be administered at a dosage of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.20 g/lb. Dosages depend, in part, on various factors including general health of the equine, weight, age, and state of nutrition. Dosages may also depend on the formulation of the composition. As a result, one of skill in the art will appreciate that the dosages described here can and will vary.

(c) Composition C

Composition C is comprised of live microorganisms, active enzymes, and optionally additional components. Each component is discussed in more detail below.

i. Live Microorganisms

Generally speaking, composition C is comprised of at least two types of live microorganisms: a yeast and a bacteria strain. Suitable yeast may include a *Saccharomyces* species, such as *Saccharomyces bayanus, Saccharomyces boulardii, Saccharomyces bulderi, Saccharomyces cariocanus, Saccharomyces cariocus, Saccharomyces cerevisiae, Saccharomyces chevalieri, Saccharomyces dairenensis, Saccharomyces ellipsoideus, Saccharomyces exiguous, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum*, or *Saccharomyces zonatus*. In an exemplary embodiment, composition C comprises *Saccharomyces cerevisiae*. Suitable yeast may also comprise yeast from species and/or genera other than *Saccharomyces*.

Composition C may comprise one, two, three or more than three yeast species. Regardless of the number of number of yeast species, the concentration of yeast in composition C is between about 400 million cfu/g to about 700 million cfu/g yeast. In one embodiment, the concentration of yeast in composition C is about 400, 500, 600, or about 700 million cfu/g. In an exemplary embodiment, the concentration of yeast in composition C is between about 500 million cfu of yeast to about 600 million cfu of yeast per gram of composition C.

Composition C is also comprised of at least one bacterial strain. Suitable bacterial strains may include a *Lactobacillus* species, an *Enterococcus* species, a *Bifidobacterium* species, a *Propionibacterium* species, a *Streptococcus* species, a *Bacillus* species, or a *Pediococcus* species.

For instance, suitable *Lactobacillus* species may include *Lactobacillus acidophilus, Lactobacillus casei, Lactobacillus salivarius, Lactobacillus plantarum, Lactobacillus Lactis, Lactobacillus rhamnosus, Lactobacillus rhamnosus, Lactobacillus pentosus, Lactobacillus reuteri, Lactobacillus crispatus, Lactobacillus johnsonii*, and *Lactobacillus equi*. In an exemplary embodiment, the *Lactobacillus* species is *Lactobacillus acidophilus*.

Suitable *Enterococcus* species may include *Enterococcus faecium, Enterococcus avium, Enterococcus durans, Enterococcus faecalis, Enterococcus faecium, Enterococcus gallinarum*, and *Enterococcus solitarius*. In an exemplary embodiment, the *Enterococcus* species is *Enterococcus faecium*.

Additionally, suitable *Bacillus* species may include *Bacillus subtilis, Bacillus pumilus*, and *Bacillus lichenformis*. Suitable *Streptococcus* species may include *Streptococcus Cremoris* or *Streptococcus Diacetilactis*. Suitable *Propionibacterium* species may include *Propionibacterium freudenreichii*. Suitable *Bifidobacterium* species may include *Bifidobacterium longum* and *Bifidobacterium lactis*. Suitable *Pediococcus* species may include *Pediococcus acidilactici*.

Composition C may comprise one, two, three, four, five, or more than five bacterial species. In an exemplary embodiment, composition C comprises at least one *Lactobacillus* species and at least one *Enterococcus* species. In a further exemplary embodiment, composition C comprises *Lactobacillus acidophilus* and *Enterococcus faecium*. When composition C comprises *Lactobacillus acidophilus*, composition C comprises between about 15 million cfu/g to about 45 million cfu/g *Lactobacillus acidophilus*. In another exemplary embodiment, composition C comprises about 20 million cfu/g to about 40 million cfu/g. In yet another exemplary embodiment, composition C comprises about 25 million cfu/g to about 35 million cfu/g. In still another exemplary embodiment, composition C comprises about 25, 26, 27, 28, 29, 30, 31, 32, 33, 34, or 35 million cfu/g.

When composition C comprises *Enterococcus faecium*, composition C comprises between about 5 million cfu/g to about 35 million cfu/g. In another exemplary embodiment, composition C comprises about 10 million cfu/g to about 30 million cfu/g. In yet another exemplary embodiment, composition C comprises about 15 million cfu/g to about 25 million cfu/g. In still another exemplary embodiment, composition C comprises about 15, 16, 17, 18, 19, 20, 21, 22, 23, 24 or 25 million cfu/g.

In a preferred embodiment, composition C comprises between about 25 million and about 35 million cfu/g *Lactobacillus acidophilus*, and between about 15 million and about 25 million cfu/g *Enterococcus faecium*.

ii. Active Enzyme

Composition C also comprises at least one active enzyme. In some embodiments, composition C comprises at least one, two, three, four, or more than four active enzymes. Suitable active enzymes include those useful for digesting nutrients, including proteases, amylases, cellulases, lipases etc. For instance, composition C may comprise a protease, an alpha-amylase, and a cellulase. Methods of producing and/or procuring such active enzymes are known in the art. For instance, the enzymes may be commercially produced, may be recombinantly produced, or may be derived from a microbial culture.

In one embodiment, composition C comprises a protease. In a preferred embodiment, composition C comprises a protease derived from an *Aspergillus* culture. Suitable *Aspergillus* species may include *Aspergillus oryzae*, *Aspergillus ficuum* (*Aspergillus niger*), or another protease producing strain of *Aspergillus*. In an exemplary embodiment, composition C comprises a protease derived from *Aspergillus oryzae*. In another exemplary embodiment, composition C comprises between about 3 HUT/g (hemoglobin units on tyrosine beads/g) to about 9 HUT/g of protease derived from *Aspergillus oryzae*. In yet another exemplary embodiment, composition C comprises between about 4 HUT/g to about 8 HUT/g of protease derived from *Aspergillus oryzae*.

In another embodiment, composition C comprises an alpha-amylase. In a preferred embodiment, composition C comprises an alpha-amylase derived from a *Bacillus* culture. Suitable *Bacillus* strains may include those listed in section I(a)i above. In an exemplary embodiment, composition C comprises an alpha-amylase from *Bacillus subtilis*. In another exemplary embodiment, composition C comprises between about 16 and about 28 MWU/g (modified Wohlgemuth units) of alpha-amylase derived from *Bacillus subtilis*. In yet another exemplary embodiment, composition C comprises between about 18 and about 26 MWU/g of alpha-amylase derived from *Bacillus subtilis*.

In yet another exemplary embodiment, composition C comprises a cellulase. In a preferred embodiment, composition C comprises a cellulase derived from a *Trichoderma* culture. Suitable *Trichoderma* strains may include *Trichoderma longibrachiatum* or *Trichoderma reesei*. In an exemplary embodiment, composition C comprises a cellulase derived from *Trichoderma longibrachiatum*. In another exemplary embodiment, composition C comprises between about 1 to about 5 CU/g (cellulase units/g) of cellulase derived from *Trichoderma longibrachiatum*. In yet another exemplary embodiment, composition C comprises between about 2 to about 4 CU/g of cellulase derived from *Trichoderma longibrachiatum*.

In an exemplary embodiment, composition C comprises a protease derived from *Aspergillus oryzae*, an alpha-amylase from *Bacillus subtillis*, and a cellulase from *Trichoderma longibrachiatum*. In a further exemplary embodiment, composition C comprises between about 4 HUT/g (hemoglobin units on tyrosine beads/g) to about 8 HUT/g of protease derived from *Aspergillus oryzae*, between about 18 to about 26 MWU/g (modified Wohlgemuth units) of alpha-amylase derived from *Bacillus subtilis*, and between about 2 to about 4 CU/g (cellulase units/g) of cellulase derived from *Trichoderma longibrachiatum*.

iii. Other Components

Composition C may further comprise fillers, binders, sweetners, smectite, anti-caking agents, natural or artificial flavorings, or similar inert ingredients. Examples of suitable fill or binding agents may include lignin-based binding agents, molasses-based binding agents, calcium bentonite binding agents, gelatins, soy-based lecithin, casein, gluten, cellulose, wheat millrun and aqueous solutions. Suitable sweeteners may include natural sweeteners such as molasses and simple sugars such as sucrose and dextrose. Artificial sweeteners such as saccharin-based sweeteners, aspartame and sorbitol (glucitol) may also be employed. Equine have shown a tolerance for vanilla, licorice, cherry, citrus and apple flavoring. However, other flavoring may also be selected if desired. Secondary flavorings may be used as enhancing agents. For example, a combination of dry flavors and oil-based flavors may be used for extended aroma properties over the course of the product's recommended shelf-life.

In some embodiments, composition C may comprise sodium calcium aluminosilicates. In other embodiments, composition C may comprise yeast cell wall extracts. For instance, composition C may comprise dried yeast fermentation solubles. In various embodiments, composition C may comprise one or more prebiotics. In one embodiment, composition C may comprise ZORIEN® Mos, manufactured by Novus® International.

As noted above, composition C also may comprise soluble fiber. Suitable sources of soluble fiber are known in the art, and non-limiting examples may include psyllium seed husk, beet pulp, and soybean hulls. In an exemplary embodiment, the soluble fiber of composition C comprises psyllium seed husk. In one embodiment, composition C comprises between about 5% and 20% by weight psyllium seed husk. For instance, composition C may comprise about 5, 6, 7, 8, 9, 10, 11, 12, 13, 14, 15, 16, 17, 18, 19, or 20% psyllium seed husk by weight.

In other embodiments, composition C may include smectite. Smectite may either be dioctahedral smectite, trioctahedral smectite or a combination of both which is commonly known as DTO Smectite (Di, Tri Octahedral). Smectite may aid in reducing detrimental bacterial toxins in the colon. In some embodiments, composition C may comprise from about 10% to about 70% by weight of smectite.

Composition C may also comprise calcium and zinc. Generally speaking, the percent calcium ranges from about 2% to about 15%. In some embodiments, the percent calcium ranges from about 5% to about 10%. The zinc concentration generally ranges from about 750 ppm to about 1250 ppm. In certain embodiments, the zinc concentration is about 900 ppm to 1100 ppm. In an exemplary embodiment, the zinc concentration is about 1000 ppm. In some embodiment, the zinc is in an inorganic compound. In preferred embodiments, the zinc is a chelate. In an especially preferred embodiment, the zinc is a methionine hydroxy analogue chelate.

In certain embodiments, composition C may also comprise licorice, anise, and vitamins, such as sodium ascorbate.

iv. Crude Analysis

Composition C comprises crude protein from at least about 2% to about 20%. In some embodiments, composition A comprises crude protein from at least about 2, 3, 4, 5, 6, 7, 8, 9, 10, 11, 12, 13, 14, 15, 16, 17, 18, 19, or 20%. In an exemplary embodiment, the crude protein is from about 3% to about 7%. Typically, composition C comprises a crude fat amount of at least about 0.5% to about 5%. In particular embodiments, composition C comprises crude fat of at least about 0.5, 1.0, 1.5, 2.0, 2.5, 3.0, 3.5, 4.0, 4.5, or 5.0%. In an exemplary embodiment, the crude fat amount is between about 0.5% and 1.5%. The crude fiber in composition C is usually between about 2% and about 15%. In certain embodiments, composition C comprises a crude fiber amount of about 2, 3, 4, 5, 6, 7, 8, 9, 10, 11, 12, 13, 14, or 15%. In an exemplary embodiment, the crude fiber amount is between about 3% and 7%.

In a particularly exemplary embodiment, composition C comprises between about 3% to about 7% crude protein, between about 0.5% and 1.5% crude fat, and between about 3% and 7% crude fiber.

v. Exemplary Embodiments

In an exemplary embodiment, composition C comprises between about 500 million cfu of yeast to about 600 million cfu of yeast per gram of composition C, between about 25 million and about 35 million cfu/g *Lactobacillus acidophilus*, between about 15 million and about 25 million cfu/g *Enterococcus faecium*, between about 4 HUT/g (hemoglobin units on tyrosine beads/g) to about 8 HUT/g of protease derived from *Aspergillus oryzae*, between about 18 to about 26 MWU/g (modified Wohlgemuth units) of alpha-amylase derived from *Bacillus subtilis*, and between about 2 to about 4 CU/g (cellulase units/g) of cellulase derived from *Trichoderma longibrachiatum*.

In a further exemplary embodiment, composition C comprises between about 500 million cfu of yeast to about 600 million cfu of yeast per gram of composition C, between about 25 million and about 35 million cfu/g *Lactobacillus acidophilus*, between about 15 million and about 25 million cfu/g *Enterococcus faecium*, between about 4 HUT/g (hemoglobin units on tyrosine beads/g) to about 8 HUT/g of protease derived from *Aspergillus oryzae*, between about 18 to about 26 MWU/g (modified Wohlgemuth units) of alpha-amylase derived from *Bacillus subtilis*, and between about 2 to about 4 CU/g (cellulase units/g) of cellulase derived from *Trichoderma longibrachiatum*, such that composition C comprises between about 3% to about 7% crude protein, between about 0.5% and 1.5% crude fat, and between about 3% and 7% crude fiber.

In yet another exemplary embodiment, composition C comprises calcium carbonate, dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, psyllium seed husk, calcium carbonate, dextrose, Brewers dried yeast, dried *Saccharomyces cerevisiae* fermentation solubles, natural and artificial flavoring, sodium ascorbate, licorice root powder, zinc methionine hydroxy analogue chelate, anise oil, and mineral oil, wherein the composition C comprises between about 500 million cfu of yeast to about 600 million cfu of yeast per gram of composition C, between about 25 million and about 35 million cfu/g *Lactobacillus acidophilus*, between about 15 million and about 25 million cfu/g *Enterococcus faecium*, between about 4 HUT/g (hemoglobin units on tyrosine beads/g) to about 8 HUT/g of protease derived from *Aspergillus oryzae*, between about 18 to about 26 MWU/g (modified Wohlgemuth units) of alpha-amylase derived from *Bacillus subtilis*, and between about 2 to about 4 CU/g (cellulase units/g) of cellulase derived from *Trichoderma longibrachiatum*, such that composition C comprises between about 3% to about 7% crude protein, between about 0.5% and 1.5% crude fat, and between about 3% and 7% crude fiber.

In a preferred embodiment, composition C comprises ASSURE GUARD® (equine digestive supplement), which is commercially available through Arenus®, a Novus International Business.

vi. Dosage and Administration

Composition C is generally administered twice a day at a dosage of between about 0.020 g/lb and about 0.1 g/lb. In some embodiments, composition C is generally administered twice a day at a dosage of about 0.020, 0.030, 0.040, 0.050, 0.060, 0.07, 0.08, 0.09, or 0.1 g/lb. In an alternative embodiment, a paste formulation of composition C may be administered at a dosage between about 0.01 g/lb to about 0.2 g/lb. For instance, a paste formulation may be administered at a dosage of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, or about 0.20 g/lb. Dosages depend, in part, on various factors including general health of the equine, weight, age, and state of nutrition. Dosages may also depend on the formulation of the composition. As a result, one of skill in the art will appreciate that the dosages described here can and will vary.

(d) Combinations

A method of the invention typically comprises either the administration of a combination of composition A and composition B, or a combination of composition A and composition C. Generally speaking, if composition A is administered in combination with composition B, then composition A should be fed in the evening, according to the dosage and administration parameters outlined in section I(a)vi above, and composition B should be fed daily in the morning, according to the dosage outlined in section I(b)vi above. Usually, if composition A is administered in combination with composition C, then composition A should be fed in the evening, according to the dosage and administration parameters outlined in section I(a)vi above, and composition C should be fed at both the morning and evening feedings according to the dosage parameters outlined in section I(c)vi above.

In certain embodiments, composition A and composition B may be combined into a single composition and fed simultaneously. In other embodiments, composition A and composition C may be combined into a single composition and fed simultaneously.

II. Methods

One aspect of the present invention encompasses methods of reducing the incidence of equine digestive disorders. In particular embodiments, the present invention provides methods of reducing the incidence of recurrent digestive disorders. Specifically, a method of the invention may be used to reduce the incidence of recurrent colic, recurrent diarrhea, ulcers, and poor body condition (including weight, hoof health, and coat health). Additionally, a method of the invention may be used to normalize intestinal motility. Each of these digestive disorders is discussed in more detail below.

(a) Recurrent Colic

One embodiment of the present invention encompasses a method of reducing the incidence of recurrent colic episodes. A "colic episode" is defined as a discrete bout of colic (abdominal pain), regardless of the length of time of the bout. Resolution of a colic episode may be determined, in part, by cessation of pain (in the absence of analgesics). Generally speaking, a colic episode may last about 2 to about 96 hours. "Recurrent colic," as used herein, refers to reoccurring colic episodes in an equine. These reoccurring colic episodes may be divided into three different patterns. The first pattern, referred to as high frequency recurrent colic, is more than one colic episode a month for at least one month. The second pattern, referred to as medium frequency recurrent colic, is at least one episode a month for at least three months. The third pattern, referred to as low frequency recurrent colic, is at least two colic episodes every six months, for more than six months.

Advantageously, a method of the invention may be used to reduce the incidence of colic episodes for all three frequency patterns (high, medium, and low). "Reducing" recurrent colic refers to reducing the number of times an equine has a colic episode in a given time frame. For a high frequency recurrent colic case, "reducing" means reducing the number of times an equine has a colic episode in a month. For a medium frequency recurrent colic case, "reducing" means reducing the number of times an equine has a colic episode in a three month time period. For a low frequency recurrent colic case, "reducing" means reducing the number of times an equine has a colic episode in a six month time period.

In certain embodiments, reducing the incidence of recurrent colic includes eliminating the recurrent colic. "Eliminating" recurrent colic refers to reducing the number of times an equine has colic in the appropriate time frame to zero (one month for high frequency, three months for medium frequency, and six months for low frequency). In one embodiment, a method of the invention may be used to reduce the incidence of colic episodes in an equine suffering from high frequency recurrent colic. In another embodiment, a method of the invention may be used to reduce the incidence of colic episodes in an equine suffering from medium frequency recurrent colic. In still another embodiment, a method of the invention may be used to reduce the incidence of colic episodes in an equine suffering from low frequency recurrent colic. In an alternative embodiment, a method of the invention may be used to eliminate the incidence of colic episodes in an equine suffering from high frequency recurrent colic. In another alternative embodiment, a method of the invention may be used to eliminate the incidence of colic episodes in an equine suffering from medium frequency recurrent colic. In still another alternative embodiment, a method of the invention may be used to eliminate the incidence of colic episodes in an equine suffering from low frequency recurrent colic.

Generally speaking, the method comprises the daily administration of a combination of Composition A and B, or composition A and C, as detailed in section I above. In one embodiment, a method of the invention encompasses administering a combination of composition A and B. In another embodiment, a method of the invention encompasses administering a combination of composition A and C. Such combinations should be administered to the equine suffering from recurrent colic for at least a week, more typically two weeks, and even more typically greater than two weeks. In one embodiment a combination of the invention is administered for at least 1, 2, 3, 4, 5, 6, 7, 8, 9, 10, 11, 12, 13, 14, 15, 16, 17, 18, 19, 20, or more than 20 weeks. In another embodiment, a combination of the invention is administered to the equine daily for the duration of a high risk colic situation, such as changing barns, changing feeds, changing water, other high stress management changes, trailering a horse, seasonal changes, or heavy exercising. In yet another embodiment, a combination of the invention is administered year round.

A method of the invention also comprises identifying an equine in need of treatment for recurrent colic. In one embodiment, "identifying" refers to what a reasonably skilled artisan would or could do to identify an equine suffering from recurrent colic—for instance, taking a health history of the equine.

Another embodiment of the present invention encompasses a method of reducing the frequency of recurrent colic episodes in an equine refractory to colic treatment. As used herein, "refractory to treatment" refers to an equine that suffers from reoccurring colic despite two or more changes to management parameters undertaken over a period of at least six months. Examples of changes to management parameters may include increasing access to water, reducing grain rations, decreasing time spent in a stall, decreasing work levels, floating teeth, reducing sand ingestion, increasing the number of feeding times per day, replacing carbohydrate based energy sources with fat based energy sources, augmenting the existing deworming program, and feeding hay before grain. Generally speaking, the method comprises the daily administration of a combination of composition A and B, or composition A and C, as detailed in section I above. Length of administration and timing of administration are detailed above.

(b) Diarrhea

Another embodiment of the present invention encompasses a method of reducing the incidence of recurrent diarrhea in an equine. As used herein, "recurrent diarrhea" is defined as diarrhea at least three times a week for at least two weeks. "Reducing" recurrent diarrhea refers to reducing the number of times an equine has diarrhea in a two week period. In certain embodiments, reducing the incidence of recurrent diarrhea includes eliminating the recurrent diarrhea. "Eliminating" recurrent diarrhea refers to reducing the number of times an equine has diarrhea in a two week period to zero. Generally speaking, the method comprises the daily administration of a combination of Composition A and B, or composition A and C, as detailed in section I above. In one embodiment, a method of the invention encompasses administering a combination of composition A and B. In another embodiment, a method of the invention encompasses administering a combination of composition A and C. Such combinations should be administered to the equine suffering from recurrent diarrhea for at least a week, more typically two weeks, and even more typically greater than two weeks. In one embodiment a combination of the invention is administered for at least 1, 2, 3, 4, 5, 6, 7, 8, 9, 10, 11, 12, 13, 14, 15, 16, 17, 18, 19, 20, or more than 20 weeks. In another embodiment, a combination of the invention is administered during known risk factors for diarrhea, such as seasonal changes, heavy exercise, trailering, or other high stress activities. In yet another embodiment a combination of the invention is administered year-round.

A method of the invention also comprises identifying an equine in need of treatment for recurrent diarrhea. In one embodiment, "identifying" refers to what a reasonably skilled artisan would or could do to identify an equine suffering from recurrent diarrhea—for instance, taking a health history of the equine.

(c) Ulcers

Still another embodiment of the present invention encompasses a method of reducing or eliminating the incidence of refractory ulcers in an equine. As used herein, a "refractory ulcer" refers to an ulcer that has not healed in response to at least one drug commonly used to treat ulcers. Suitable drugs may include H2 blockers (e.g. cimetidine and ranitidine), proton pump inhibitors (e.g. omeprazole), buffers, and protectants (e.g. sucralfate and other drugs that block acid from contacting the stomach lining). "Reducing" the incidence of refractory ulcers in an equine refers to reducing the symptoms of an ulcer. Such symptoms may include poor appetite, weight loss and poor body condition, poor hair coat, mild colic, mental dullness or attitude changes, poor performance, loose stools, and lying down more than normal. In a foal, the symptoms may also comprise teeth grinding, excessive salivation, diarrhea, and lying on the back. In certain embodiments, reducing the incidence of refractory ulcers includes eliminating the refractory ulcers. "Eliminating" the incidence of refractory ulcers refers to no evidence of an ulcer via a gastroduodenoscopy in one embodiment, and sessation of symptoms of an ulcer in another embodiment.

Generally speaking, the method comprises the daily administration of a combination of composition A and B, or composition A and C, as detailed in section I above. In one embodiment, a method of the invention encompasses administering a combination of composition A and B. In another embodiment, a method of the invention encompasses administering a combination of composition A and C. Such combinations should be administered to the equine suffering from gastric ulcers for at least a week, more typically two weeks, and even more typically greater than two weeks. In one embodiment a combination of the invention is administered for at least 1, 2, 3, 4, 5, 6, 7, 8, 9, 10, 11, 12, 13, 14, 15, 16, 17, 18, 19, 20, or more than 20 weeks. In another embodiment, a combination of the invention is administered during known risk factors for ulcers, such as seasonal changes, heavy exercise, trailering, or other high stress activities. In yet another embodiment a combination of the invention is administered year-round.

A method of the invention also comprises identifying an equine in need of treatment for an ulcer. In one embodiment, "identifying" refers to what a reasonably skilled artisan would or could do to identify an equine suffering from an ulcer—for instance, taking a health history of the equine.

(d) Poor Body Condition

Yet another embodiment of the present invention encompasses a method of improving body condition. As used herein, "body condition" refers to weight (including anorexia), hoof health, and coat health. "Improving" body condition refers to increasing weight, increasing hoof growth and/or increasing hoof strength, and improving coat quality.

Generally speaking, the method comprises the daily administration of a combination of composition A and B, or composition A and C, as detailed in section I above. In one embodiment, a method of the invention encompasses administering a combination of composition A and B. In another embodiment, a method of the invention encompasses administering a combination of composition A and C. Such combinations should be administered to the equine suffering from poor body condition for at least a week, more typically two weeks, and even more typically greater than two weeks. In one embodiment a combination of the invention is administered for at least 1, 2, 3, 4, 5, 6, 7, 8, 9, 10, 11, 12, 13, 14, 15, 16, 17, 18, 19, 20, or more than 20 weeks. In another embodiment, a combination of the invention is administered during known high-stress activities or time frames (e.g. heavy work or season change). In yet another embodiment a combination of the invention is administered year-round.

(e) Normalizing Intestinal Motility

A further embodiment of the invention encompasses a method for normalizing intestinal motility in an equine. Generally speaking, two to three strong intestinal contractions per minute is considered ideal motility. As those skilled in the art understand, however, this can vary from horse to horse. Contraction rates may be determined by auscultation.

Hypermotility in an equine may lead to digestive disorders, such as diarrhea. As such, in one embodiment, a method of in the invention comprises reducing intestinal motility in a hypermotile equine. "Reducing" hypermotility refers to decreasing the average number of intestinal contractions per minute for a particular equine. Hypomotility in a horse may also lead to digestive disorders in an equine, such as colic. In another embodiment, a method of the invention comprises increasing intestinal motility in a hypomotile equine. "Increasing" hypomotility refers to increasing the average number of intestinal contractions per minute for a particular equine.

Generally speaking, the method comprises the daily administration of a combination of composition A and B, or composition A and C, as detailed in section I above. In one embodiment, a method of the invention encompasses administering a combination of composition A and B. In another embodiment, a method of the invention encompasses administering a combination of composition A and C. Such combinations should be administered to the equine suffering hypermotility or hypomotility for at least a week, more typically two weeks, and even more typically greater than two weeks. In one embodiment a combination of the invention is administered for at least 1, 2, 3, 4, 5, 6, 7, 8, 9, 10, 11, 12, 13, 14, 15, 16, 17, 18, 19, 20, or more than 20 weeks. In another embodiment, a combination of the invention is administered during known high-stress activities or time frames (e.g. heavy work or season change). In yet another embodiment a combination of the invention is administered year-round.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

DEFINITIONS

As used herein, "equine" refers to a member of the genus *Equus*, including *E. africanus*, *E. ferus*, *E. ferus caballus*, *E. grevyi*, *E. hemionus*, *E. kiang*, *E. quagga*, and *E. zebra*. In an exemplary embodiment, "equine" refers to *E. ferus caballus*.

EXAMPLES

The following examples illustrate various iterations of the invention.

Example 1

Clinical Study Design

Independent equine veterinary practitioners were given the ability to enroll up to three equine cases with digestive disorders in a clinical study. Sixty-four veterinarians volunteered 144 cases for the study, where the horses were fed either a combination of composition A and composition B (e.g. ASSURE PLUS® and ASSURE®) or a combination of composition A and composition C (e.g. ASSURE PLUS® and ASSURE GUARD®). The independent practitioners submitted case histories, monitored the feeding protocol with the owners, reviewed owner weekly worksheets and logs, and performed independent evaluations of the results. Cases were submitted from all areas of the United States and there was no screening for geography or weather conditions. Horses over 24 years of age were excluded, as were horses that had undergone prior colic surgery, horses suffering with a primary medical issue that might be the cause of digestive upset, and horses suspected or confirmed to have enteroliths. The owners were not required to change any of the daily activities with their horses and were encouraged not to make any feeding protocol changes. Horses that were on a digestive supplement were required to discontinue use of the supplement. Each horse enrolled was categorized with a primary as well as up to two secondary conditions.

Upon completion of the evaluation period, the veterinarians submitted the evaluation forms to a researcher at North Carolina State University for auditing and statistical analysis. Six indications were evaluated—recurrent diarrhea, recurrent colic, gastric ulcers, sand accumulation, anorexia, and weight loss or poor condition.

Example 2

Recurrent Colic

In a clinical trial investigating six different indications, thirty different horses were enrolled for recurrent colic. The treatment consisted of administration of either the combination of composition A and composition B (e.g. ASSURE PLUS® and ASSURE®) or the combination of composition A and composition C (e.g. ASSURE PLUS® and ASSURE GUARD®). The individual results are detailed below. In summary, of thirty cases, twenty-seven (90%) were reported as completely resolved. The remaining three cases (10%) were reported as partially resolved based on a decrease in frequency of colic bouts. In each case, the veterinarian reported that prior treatment attempts had been unsuccessful.

High Frequency Recurrent Colic

Of the thirty recurrent colic cases, seven were categorized as high frequency, meaning more than one colic episode per month for at least one month. Of these seven cases, a method of the invention eliminated the recurrent colic in five instances, and reduced the recurrent colic in two instances. The results are summarized in Table 1 below, and each individual case is detailed below.

TABLE 1

| | Recurrent Colic - High Frequency | | | | | | |
|---|---|---|---|---|---|---|---|
| Name of Horse | Length of time Horse had greater than one colic episode per month | Breed Gender Age | Treatment | Weeks of Treatment | Time to Response | Colic completely resolved | Colic frequency reduced |
| King | >2 yrs | QH G 5-18 yrs | Assure ® and Assure Plus ® | 10 | 2-3 weeks | No | Yes |
| Ollie | 6 months-2 yrs | THB G 5-18 yrs | Assure Guard ® and Assure Plus ® | 8 | Less than one week | Yes | n/a |
| Chance | 6 months-2 yrs | Welsh X G 5-18 yrs | Assure ® and Assure Plus ® | 8 | 1-2 weeks | Yes | n/a |
| Willis | 3-6 months | WHBXTHB G 2-5 yrs | Assure Guard ® and Assure Plus ® | 12 | Hard to determine | Yes | n/a |
| Peaceful T | 3-6 months | THB M 2-5 yrs | Assure Guard ® and Assure Plus ® | 6 | 2-3 weeks | No | Yes |
| Marilyn | 1-3 months | QH M 5-18 yrs | Assure ® and Assure Plus ® | 12 | 1-2 weeks | Yes | n/a |
| Kabulina | 1-3 months | Paso M 5-18 yrs | Assure Guard ® and Assure Plus ® | 16 | 2-3 weeks | Yes | n/a |

King

King is a quarter horse gelding, between 18 and 24 yrs old, that suffered from high frequency recurrent colic for more than two years. After two to three weeks of treatment with ASSURE® and ASSURE PLUS®, King saw a reduction in the incidence of colic episodes.

Ollie

Ollie is a thoroughbred gelding, between 5 and 18 yrs old, that suffered from high frequency recurrent colic for at least six months. After less than one week of treatment with ASSURE GUARD® and ASSURE PLUS®, Ollie's recurrent colic was eliminated.

Chance

Chance is a Welsh cross gelding, between 5 and 18 yrs old, that suffered from high frequency recurrent colic for at least six months. After one to two weeks of treatment with ASSURE® and ASSURE PLUS®, Chance's recurrent colic was eliminated.

Willis

Willis, a gelding, is a warmblood thoroughbred cross between 2 and 5 years old. Willis suffered from high frequency recurrent colic for at least three months prior to treatment, and averaged more than one colic episode a month. Willis was treated with ASSURE PLUS® and ASSURE GUARD® for twelve weeks, which eliminated Willis's recurrent colic.

Peaceful T

Peaceful T is a thoroughbred mare between 2 and 5 years old. Peaceful T suffered from high frequency recurrent colic for at least three months prior to treatment. After treatment with ASSURE GUARD® and ASSURE PLUS® for two to three weeks, Peaceful T saw a reduction in the number of recurrent colic episodes per month.

Marilyn

Marilyn is a quarter horse mare between 5 and 18 years old. Marilyn suffered from high frequency recurrent colic for at least one month prior to treatment. After treatment with ASSURE® and ASSURE PLUS® for one to two weeks, Marilyn's recurrent colic was eliminated.

Kabulina

Kabulina is a Paso mare between 5 and 18 years old. Kabulina suffered from high frequency recurrent colic for at least a month, while pregnant. After treatment with ASSURE GUARD® and ASSURE PLUS® for two to three weeks, Kabulina's recurrent colic was eliminated, and she eventually gave birth to a healthy foal.

Medium Frequency Recurrent Colic

Of the thirty recurrent colic cases, four were categorized as medium frequency, meaning at least one colic episode per month for at least three months. In all four cases, a method of the invention eliminated the recurrent colic. The results are summarized in Table 2 below, and each individual case is detailed below.

TABLE 2

Recurrent Colic - Medium Frequency

| Name of Horse | Length of Time Horse has had at least one colic episode a month | Breed Gender Age | Treatment | Weeks of Treatment | Time to Response | Colic Completely Resolved |
|---|---|---|---|---|---|---|
| Cherokee | >2 years | Appaloosa G 18-24 yrs | Assure Guard ® and Assure Plus ® | 6 | 1-2 weeks | Yes |
| Winston | 6 months to 2 years | QH/WHBG 5-18 yrs | Assure Guard ® and Assure Plus ® | 16 | 3-4 weeks | Yes |
| Icaus | 3 months to 6 months | THB G 5-18 yrs | Assure Guard ® and Assure Plus ® | 12 | >6 weeks | Yes |
| Major | 3 months to 6 months | Paint G 5-18 yrs | Assure ® and Assure Plus ® | 12 | undetermined | Yes |

Cherokee

Cherokee is a quarter horse gelding between 18 and 24 years old. Cherokee suffered from medium frequency recurrent colic for at least 2 years prior to treatment. After treatment with ASSURE GUARD® and ASSURE PLUS® for one to two weeks, Cherokee's recurrent colic was eliminated.

Winston

Winston is a Quarter horse/Warmblood gelding between 5 and 18 years old. Winston suffered from medium frequency recurrent colic for at least six month prior to treatment with ASSURE GUARD® and ASSURE PLUS®. After three to four weeks of treatment, Winston's recurrent colic was eliminated.

Icaus

Icaus is a thoroughbred gelding between 5 and 18 years old. Icaus suffered from medium frequency recurrent colic for at least three months prior to treatment with ASSURE GUARD® and ASSURE PLUS®. After six weeks of treatment, Icaus's recurrent colic was eliminated.

Major

Major is a paint gelding between 5 and 18 years old. Major suffered from medium frequency recurrent colic for at least three months prior to treatment with ASSURE® and ASSURE PLUS®. After twelve weeks of treatment, Major's recurrent colic was eliminated.

Low Frequency Recurrent Colic

Of the thirty recurrent colic cases, six were categorized as low frequency, meaning at least two colic episodes every six months. In five of the six cases, a method of the invention eliminated the recurrent colic. In the remaining case, a method of the invention reduced the frequency of colic episodes. The results are summarized in Table 3 below, and each individual case is detailed below.

TABLE 3

Recurrent Colic - Low Frequency

| Name of Horse | Length of Time Horse has had at least two colic episodes in six months | Breed Gender Age | Treatment | Weeks of Treatment | Time to Response | Colic Completely Resolved | Colic Frequency Reduced |
|---|---|---|---|---|---|---|---|
| Claire | >2 years | Mustang M 5-18 yrs | Assure ® and Assure Plus ® | 16 | 1-2 weeks | Yes | n/a |
| Blondie | 6 months-2 years | Shetland M 5-18 yrs | Assure Guard ® and Assure Plus ® | 16 | >6 weeks | No | Yes |
| Lex | 6 months-2 years | THB G 2-5 yrs | Assure Guard ® and Assure Plus ® | 16 | undetermined | Yes | n/a |
| Cinnamon | 6 months-2 years | Pony G 5-18 yrs | Assure ® and Assure Plus ® | 8 | <1 week | Yes | n/a |
| Titok | 6 months-2 years | THBX G 5-18 yrs | Assure ® and Assure Plus ® | 4 | 1-2 week | Yes | n/a |
| Prada | 6 months-2 years | WHB M 5-18 yrs | Assure ® and Assure Plus ® | 12 | 3-4 weeks | Yes | n/a |

Claire

Claire is a mustang mare between 5 and 18 years old. Claire suffered from low frequency recurrent colic for more than two years prior to treatment with ASSURE® and ASSURE PLUS®. After one to two weeks of treatment, Claire's recurrent colic was eliminated.

Blondie

Blondie is a Shetland mare between 5 and 18 years old. Blondie suffered from low frequency recurrent colic for at least six months prior to treatment with ASSURE GUARD® and ASSURE PLUS®. After about six weeks of treatment, Blondie saw a reduction in the incidence of colic episodes.

Lex

Lex is a thoroughbred gelding between 2 and 5 years old. Lex suffered from low frequency recurrent colic for at least six months prior to treatment with ASSURE GUARD® and ASSURE PLUS®. After about sixteen weeks of treatment, Lex's recurrent colic was eliminated.

Cinnamon

Cinnamon is a pony gelding between 5 and 18 years old. Cinnamon suffered from low frequency recurrent colic for at least six months prior to treatment with ASSURE® and ASSURE PLUS®. After less than about 1 week, Cinnamon's recurrent colic was eliminated.

Titok

Titok is a thoroughbred cross gelding between 5 and 18 years old. Titok suffered from low frequency recurrent colic for at least six months prior to treatment with ASSURE® and ASSURE PLUS®. After about one to two weeks, Titok's recurrent colic was eliminated.

Prada

Prada is a warmblood mare between 5 and 18 years old. Prada suffered from low frequency recurrent colic for at least six months prior to treatment with ASSURE® and ASSURE PLUS®. After about three to four weeks, Prada's recurrent colic was eliminated.

Example 3

Diarrhea

In a clinical trial investigating six different indications, forty-two different horses were primarily enrolled for recurrent diarrhea. The treatment consisted of administration of either the combination of composition A and composition B (e.g. ASSURE PLUS® and ASSURE®) or the combination of composition A and composition C (e.g. ASSURE PLUS® and ASSURE GUARD®). The individual results are detailed below. In summary, of forty-two cases where recurrent diarrhea was reported as the primary indication, twenty-four (57%) cases were reported as completely resolved and twelve (29%) cases were reported as partially resolved. Combined, a method of the invention reduced or eliminated recurrent diarrhea in 86% of the cases investigated. These cases are summarized in Table 4 below.

Including secondary and tertiary indication, fifty-four cases of diarrhea were reported. Of these fifty-four, 56% of the cases were completely resolved, and 24% of the cases were partially resolved.

TABLE 4

Summary of diarrhea cases

| Name of Horse | Treatment | Weeks of Treatment | Time to Response | Diarrhea Completely Resolved | Diarrhea Frequency Reduced |
|---|---|---|---|---|---|
| Salty | Assure ® and Assure Plus ® | 5 | 2-3 Weeks | No | Yes |
| Wally | Assure ® and Assure Plus ® | 6 | 4-6 Weeks | No | Yes |

TABLE 4-continued

Summary of diarrhea cases

| Name of Horse | Treatment | Weeks of Treatment | Time to Response | Diarrhea Completely Resolved | Diarrhea Frequency Reduced |
|---|---|---|---|---|---|
| Maestoso | Assure Guard ® and Assure Plus ® | 6 | 2-3 Weeks | Yes | n/a |
| Pal-o-mine | Assure ® and Assure Plus ® | 4 | | No | No |
| Lady | Assure ® and Assure Plus ® | 8 | 1-2 Weeks | Yes | n/a |
| Daisy | Assure ® and Assure Plus ® | 6 | <1 Week | Yes | n/a |
| General Reunion | Assure ® and Assure Plus ® | 6 | 3-4 Weeks | Yes | n/a |
| Material Girl | Assure Guard ® and Assure Plus ® | 4 | | No | n/a |
| Dlighted | Assure ® and Assure Plus ® | 8 | | No | No |
| Emma | Assure ® and Assure Plus ® | 8 | 2-3 Weeks | Yes | n/a |
| Incitato | Assure Guard ® and Assure Plus ® | 6 | 3-4 Weeks | Yes | n/a |
| Regal | Assure ® and Assure Plus ® | 4 | | No | No |
| Big | Assure ® and Assure Plus ® | 4 | 2-3 Weeks | No | Yes |
| Gus | Assure ® and Assure Plus ® | 4 | 1-2 Weeks | No | Yes |
| Cabaret | Assure ® and Assure Plus ® | 6 | <1 Week | Yes | n/a |
| McKayla | Assure ® and Assure Plus ® | 6 | 2-3 Weeks | No | Yes |
| Desantos | Assure Guard ® and Assure Plus ® | 6 | 2-3 Weeks | Yes | n/a |
| Star | Assure ® and Assure Plus ® | 6 | 2-3 Weeks | Yes | n/a |
| BonVivant | Assure ® and Assure Plus ® | 6 | 3-4 Weeks | No | Yes |
| Beau | Assure ® and Assure Plus ® | 6 | <1 Week | No | Yes |
| Emma (2) | Assure ® and Assure Plus ® | 8 | 2-3 Weeks | Yes | n/a |
| LuLu | Assure Guard ® and Assure Plus ® | 8 | 2-3 Weeks | Yes | n/a |
| Smokey | Assure Guard ® and Assure Plus ® | 8 | 2-3 Weeks | Yes | n/a |
| Brown Eyed Mr. | Assure ® and Assure Plus ® | 8 | 3-4 Weeks | No | Yes |
| MoJo | Assure ® and Assure Plus ® | 8 | 2-3 Weeks | Yes | n/a |
| Indy | Assure ® and Assure Plus ® | 6 | 3-4 Weeks | No | Yes |
| Claire | Assure ® and Assure Plus ® | 16 | 1-2 Weeks | No | Yes |
| James | Assure ® and Assure Plus ® | 7 | 2-3 Weeks | Yes | n/a |
| Speedy Remedy | Assure ® and Assure Plus ® | 4 | <1 Week | No | Yes |
| Banjo | Assure Guard ® and Assure Plus ® | 4 | | No | No |
| Squirt | Assure ® and Assure Plus ® | 8 | 3-4 Weeks | No | No |
| Ugoita B Catty | Assure ® and Assure Plus ® | 6 | 3-4 Weeks | No | Yes |
| Dupree | Assure ® and Assure Plus ® | 8 | <1 Week | Yes | n/a |
| Titan | Assure Guard ® and Assure Plus ® | 6 | 1-2 Weeks | Yes | n/a |
| Oreo | Assure ® and Assure Plus ® | 12 | 1-2 Weeks | Yes | n/a |
| Major | Assure ® and Assure Plus ® | 8 | 2-3 Weeks | Yes | n/a |
| Cinnamon | Assure ® and Assure Plus ® | 8 | <1 Week | Yes | n/a |
| BabyDoc | Assure ® and Assure Plus ® | 7 | 2-3 Weeks | Yes | n/a |
| Pucci | Assure ® and Assure Plus ® | 6 | 4-6 Weeks | Yes | n/a |
| Granite | Assure ® and Assure Plus ® | 6 | 1-2 Weeks | Yes | n/a |
| Cedarell Ben | Assure ® and Assure Plus ® | 7 | 1-2 Weeks | Yes | n/a |
| Hope | Assure ® and Assure Plus ® | 5 | 2-3 Weeks | Yes | n/a |
| Sadie | Assure ® and Assure Plus ® | 8 | <1 Week | n/a | Yes |

Example 4

Ulcers

In a clinical trial investigating six different indications, thirty-three different horses were enrolled for suspected ulcers. The ulcers may be gastric or colonic. The treatment consisted of administration of either the combination of composition A and composition B (e.g. ASSURE PLUS® and ASSURE®) or the combination of composition A and composition C (e.g. ASSURE PLUS® and ASSURE GUARD®). Of these, 48% were reported as completely resolved and 33% were reported as partially resolved. Combined, a method of the invention reduced or eliminated ulcers in 81% of the cases investigated.

Ulcer cases were not required to have gastroscopy confirmation of ulcers. Although some were confirmed by gastroscopy, others were suspected based upon either trial therapy or clinical signs. The evaluations were based upon signs of ulcers, including behavior, weight and condition, eating habits and attitude.

Of the 33 cases studied for suspected ulcers, seven were also receiving some prescription medication for gastric ulcers during the trial period. The veterinarians were asked to begin the clinical study once they felt their patient had stabilized in clinical improvement with any prescription treatment. This study design encompassed evaluation of any addition benefits seen with treatment using a method of the invention.

Some of the ulcer cases are detailed in Table 5 below.

TABLE 5

Ulcers

| Name of Horse | Treatment | Weeks of Treatment | Time to Response | Gastric Ulcers Completely Resolved | Gastric Ulcers Frequency Reduced |
|---|---|---|---|---|---|
| Blondie | Assure Guard ® and Assure Plus ® | 16 | >6 Weeks | No | Yes |
| Mowgli | Assure Guard ® and Assure Plus ® | | | Yes | n/a |
| Patches | Assure Guard ® and Assure Plus ® | 6 | 1-2 Weeks | UK* | Yes |
| Actor | Assure Guard ® and Assure Plus ® | 4 | 1-2 Weeks | UK | Yes |
| Loprete | Assure Guard ® and Assure Plus ® | 7 | 1-2 Weeks | UK | UK |
| Amigo | Assure Guard ® and Assure Plus ® | 7 | 2-3 Weeks | UK | UK |
| Dan Me Hot | Assure Guard ® and Assure Plus ® | 6 | <1 Week | No | Yes |
| Chummy | Assure Guard ® and Assure Plus ® | 6 | >6 Weeks | No | No |
| Beau | Assure Guard ® and Assure Plus ® | 8 | 1-2 Weeks | UK | UK |
| Willis | Assure Guard ® and Assure Plus ® | 12 | | Yes | n/a |
| Ramanya | Assure Guard ® and Assure Plus ® | 8 | 2-3 Weeks | Yes | n/a |
| Frosty | Assure Guard ® and Assure Plus ® | 6 | 1-2 Weeks | Yes | n/a |

*UK—unknown

Example 5

Body Condition

Fifty-four cases of weight loss or poor condition were enrolled in the clinical study. The treatment consisted of administration of either the combination of composition A and composition B (e.g. ASSURE PLUS® and ASSURE®) or the combination of composition A and composition C (e.g. ASSURE PLUS® and ASSURE GUARD®). Of these, 61% were reported as completely resolved, while 33% were reported as partially resolved. Combined, a method of the invention improved body condition in 94% of the cases reported.

What is claimed is:

1. A method for reducing the incidence of recurrent colic refractory to treatment in an equine, the method comprising
   a. identifying an equine in need of treatment for recurrent colic refractory to treatment, and
   b. administering a combination of composition A and composition B to the equine, or a combination of composition A and composition C to the equine, wherein
      i. composition A comprises at least about 60% soluble fiber, yeast, a live *Lactobacillus* species, and a live *Enterococcus* species,
      ii. composition B comprises yeast, a live *Lactobacillus* species, a live *Enterococcus* species, a protease, a cellulase, and an alpha-amylase; and
      iii. composition C comprises yeast, a live *Lactobacillus* species, a live *Enterococcus* species, and calcium.

2. The method of claim 1, wherein
   a. composition A comprises between about 75 million cfu of yeast to about 85 million cfu of yeast per gram of composition A, between about 2 million and about 10 million cfu/g *Lactobacillus* acidophilus, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber; and
   b. composition B comprises composition B comprises between about 1000 million cfu of yeast to about 1200 million cfu of yeast per gram of composition A, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7 CU/g (cellulase units/g) of cellulase derived from *Trichoderma longibrachiatum*, and psyllium seed husk, such that composition B comprises between about 6% to about 10% crude protein, between about 0.5% and 1.5% crude fat, and between about 4% and 8% crude fiber.

3. The method of claim 1, wherein
   a. composition A comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber; and b. composition C comprises between about 500 million cfu of yeast to about 600 million cfu of yeast per gram of composition C, between about 25 million and about 35 million cfu/g *Lactobacillus acidophilus*, between about 15 million and about 25 million cfu/g *Enterococcus faecium*, between about 4 HUT/g (hemoglobin units on tyrosine beads/g) to about 8 HUT/g of protease derived from *Aspergillus oryzae*, between about 18 to about 26 MWU/g (modified Wohlgemuth units) of alpha-amylase derived from *Bacillus subtilis*, and between about 2 to about 4 CU/g (cellulase units/g) of cellulase derived from *Trichoderma longibrachiatum*, such that composition C comprises between about 3% to about 7% crude protein, between about 0.5% and 1.5% crude fat, and between about 3% and 7% crude fiber.

4. The method of claim 1, wherein the recurrent colic refractory to treatment is eliminated.

5. The method of claim 1, wherein composition A is fed in the evening and composition B is fed in the morning.

6. The method of claim 1, wherein composition A is fed daily for about five weeks, and then alternately not fed for three weeks and fed for a week.

7. The method of claim 1, wherein composition A comprises psyllium seed husk, wheat mill run, molasses, dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, Brewers dried yeast, dried *Saccharomyces cerevisiae* fermentation solubles, and natural and artificial flavoring.

8. The method of claim 1, wherein composition B comprises dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, Brewers dried yeast, dried *Saccharomyces cerevisiae* fermentation solubles, psyllium seed husk, and natural and artificial flavoring.

9. The method of claim 1, wherein the recurrent colic is high frequency recurrent colic.

10. The method of claim 1, wherein the recurrent colic is medium frequency recurrent colic.

11. The method of claim 1, wherein the recurrent colic is low frequency recurrent colic.

12. The method of claim 1, wherein composition A is fed in the evening and composition C is fed in the morning and the evening.

13. The method of claim 1, wherein composition C comprises calcium carbonate, dried *Saccharomyces cerevisiae* fermentation product, sodium silicoaluminate, dried *Lactobacillus acidophilus* fermentation product, dried *Enterococcus faecium* fermentation product, dried *Aspergillus oryzae* fermentation extract, dried *Trichoderma longibrachiatum* fermentation extract, dried *Bacillus subtilis* fermentation extract, psyllium seed husk, calcium carbonate, dextrose, Brewers dried yeast, dried *Saccharomyces cerevisiae* fermentation solubles, natural and artificial flavoring, sodium ascorbate, licorice root powder, zinc methionine hydroxy analogue chelate, anise oil, and mineral oil.

14. A method for reducing the incidence of recurrent diarrhea in an equine, the method comprising
 a. identifying an equine in need of treatment for recurrent diarrhea, and
 b. administering a combination of composition A and composition B to the equine, or a combination of composition A and composition C to the equine, wherein
  i. composition A comprises at least about 60% soluble fiber, yeast, a live *Lactobacillus* species, and a live *Enterococcus* species,
  ii. composition B comprises yeast, a live *Lactobacillus* species, a live *Enterococcus* species, a protease, a cellulase, and an alpha-amylase; and
  iii. composition C comprises yeast, a live *Lactobacillus* species, a live *Enterococcus* species, and calcium.

15. A method of claim 14, wherein
 a. composition A comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber; and
 b. composition B comprises composition B comprises between about 1000 million cfu of yeast to about 1200 million cfu of yeast per gram of composition A, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7 CU/g (cellulase units/g) of cellulase derived from *Trichoderma longibrachiatum*, and psyllium seed husk, such that composition B comprises between about 6% to about 10% crude protein, between about 0.5% and 1.5% crude fat, and between about 4% and 8% crude fiber.

16. A method for normalizing intestinal motility in an equine, the method comprising
 a. identifying an equine in need of treatment for intestinal hypermotility or hypomotility, and
 b. administering a combination of composition A and composition B to the equine, or a combination of composition A and composition C to the equine, wherein
  i. composition A comprises at least about 60% soluble fiber, yeast, a live *Lactobacillus* species, and a live *Enterococcus* species, ii. composition B comprises yeast, a live *Lactobacillus* species, a live *Enterococcus* species, a protease, a cellulase, and an alpha-amylase; and iii. composition C comprises yeast, a live *Lactobacillus* species, a live *Enterococcus* species, and calcium.

17. The method of claim 16, wherein a. composition A comprises between about 75 million cfu of yeast to about 85 million cfu of yeast per gram of composition A, between about 2 million and about 10 million cfu/g *Lactobacillus acidophilus*, between about 2 million and about 10 million cfu/g *Enterococcus faecium*, between about 0.8 HUT/g (hemoglobin units on tyrosine beads/g) to about 1.2 HUT/g of protease derived from *Aspergillus oryzae*, between about 2.5 to about 3.5 MWU/g (modified Wohlgemuth units) of alpha-amylase derived from *Bacillus subtilis*, between about 0.2 to about 0.6 CU/g (cellulase units/g) of cellulase derived from *Trichoderma longibrachiatum*, and psyllium seed husk, such that composition A comprises between about 2% to about 6% crude protein, between about 0.5% and 1.5% crude fat, and between about 6% and 10% crude fiber; and b. composition B comprises composition B comprises between about 1000 million cfu of yeast to about 1200 million cfu of yeast per gram of composition A, between about 60 million and about 70 million cfu/g *Lactobacillus acidophilus*, between about 40 million and about 50 million cfu/g *Enterococcus faecium*, between about 12 HUT/g (hemoglobin units on tyrosine beads/g) to about 14 HUT/g of protease derived from *Aspergillus oryzae*, between about 40 to about 50 MWU/g (modified Wohlgemuth units) of alpha-amylase derived from *Bacillus subtilis*, between about 5 to about 7 CU/g (cellulase units/g) of cellulase derived from *Trichoderma longibrachiatum*, and psyllium seed husk, such that composition B comprises between about 6% to about 10% crude protein, between about 0.5% and 1.5% crude fat, and between about 4% and 8% crude fiber.

\* \* \* \* \*